June 19, 1973 D. L. ARMSTRONG Plant Pat. 3,360
PEACH TREE
Filed June 4, 1971
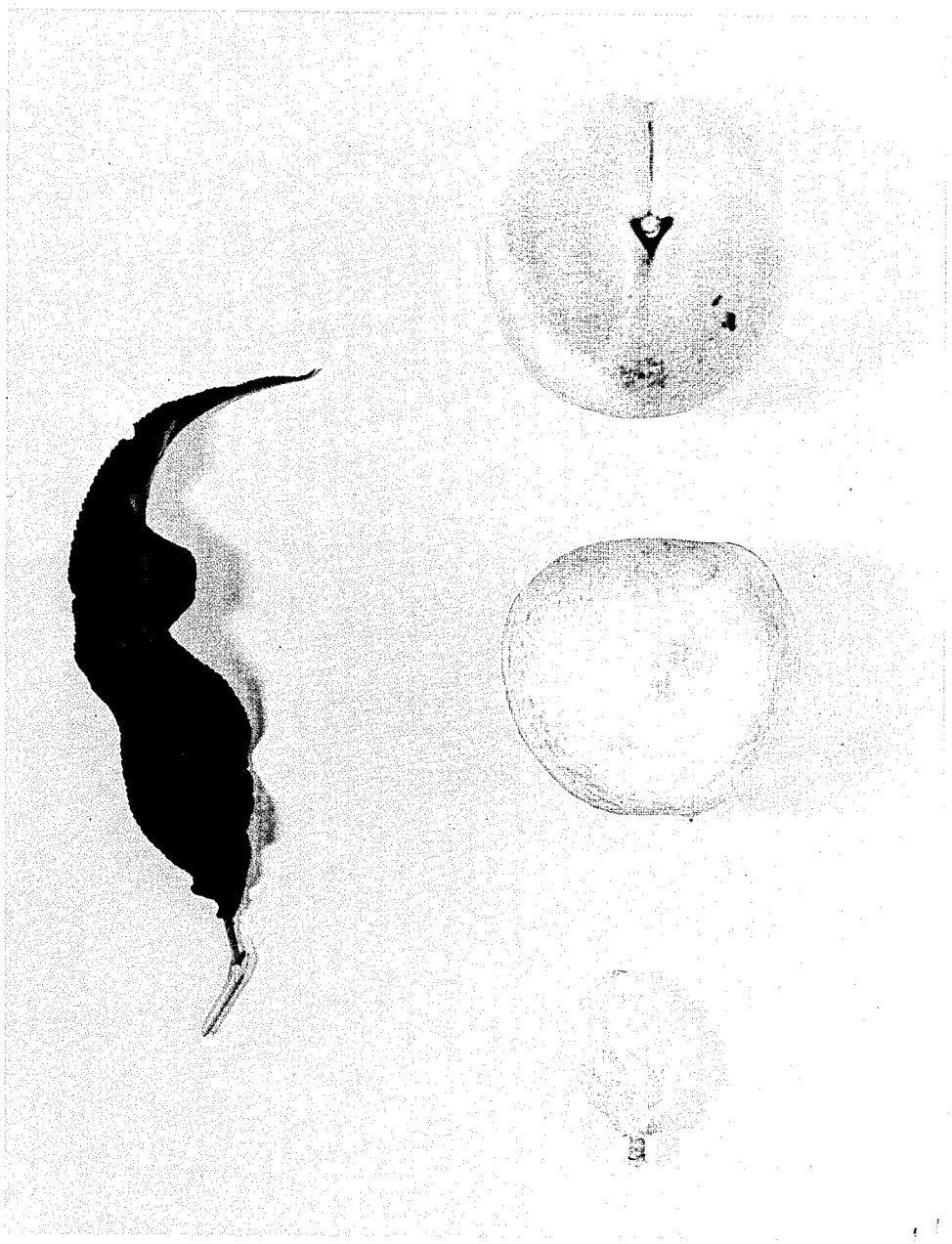

United States Patent Office

Plant Pat. 3,360
Patented June 19, 1973

3,360
PEACH TREE

David L. Armstrong, Upland, Calif., assignor to Armstrong Nurseries, Inc., Ontario, Calif.

Filed June 4, 1971, Ser. No. 150,246
Int. Cl. A01h 5/03
U.S. Cl. Plt.—43 1 Claim

ABSTRACT OF THE DISCLOSURE

A peach tree characterized in its tendency to bear large crops of fruits which ripen quite early, namely, during the latter half of the month of May in Wasco, Calif. The habit of growth is fairly vigorous; the leaves are rather long and distinctly wavy and crinkled. The leaves bear a mixture of globose and reinform glands both on the petiole and on the margin of the leaf just above the petiole. The fruit is yellow-fleshed with little or no red coloration. The flesh, which is of melting texture, adheres closely to the stone until the fruit is fully ripe, and then loosens somewhat. The fruits are about ten percent larger than comparable varieties ripening in the same time interval, even though they are nearly ten percent smaller in diameter than some of the later-ripening varieties.

This invention relates to the discovery and asexual reproduction of a new variety of peach, the fruit of which has yellow flesh which adheres closely to the stone until fully mature. The tree bears heavily, and very early in the season, having fruits which are larger than one usually encounters in varieties which ripen so early. It ripens, in Wasco, Calif., during the latter half of the month of May.

The fruits display substantial red mottling and/or blush on a yellow skin which has a slight greenish tinge at the bottom of the stem cavity. The fruits are symmetrical and uniform in shape, being generally globose or nearly round, with little or no beak at the apex, and with the suture prominent only at the base. These fruits are yellow-fleshed, with little or no trace of red in the fleshy part, even at the stone. The stone adheres rather tightly to the flesh until the fruit is fully ripe, when it becomes paritally free. The fruit is melting of good quality, firmness and flavor, approaching, in these respects, the mid-season types of peaches. On the average, the peaches are about 10% larger than the "Armgold" peaches, to which variety this new cultivar is comparable, both in ripening season and in winter chilling requirement.

The variety was originally propagated and asexually reproduced by David L. Armstrong in Wasco, Calif. The description which follows will relate to a tree grown in that area. The properties to be described will be reproduced through successive propagations by budding. The seed parent was an unnamed seedling, "Flamingo"×"Springtime," and the pollen parent was "June Gold."

Among the characteristics which distinguish this variety of peach tree from its seed parent may be noted the following:

The fruit of this new variety ripens three to four weeks earlier than that of the seed parent, which was an unnamed and unintroduced seedling derived from Flamingo×Springtime.

The flesh of this new variety adheres more closely to the stone than does the flesh of its seed parent.

On the average, the fruit of this new variety is about ten percent smaller in diameter than is the fruit of its seed parent.

Some of the differences which may be noted between this new variety and its pollen parent, June Gold, are as follows:

The fruit of this new variety has substantially less red in the flesh than does the fruit of its pollen parent.

The flesh of this new variety adheres more closely to the stone than that of its pollen parent.

The fruit of this new variety is approximately five percent smaller in diameter, on the average, than that of its pollen parent, and this fruit ripens from one to two weeks earlier.

Referring to the varietal identification technique as established by Meader & Blake [1], the foliage of this new variety would be considered Class IV, distinctly wavy and crinkled, whereas the pollen parent has foliage that would be considered Class II, or "wavy."

The accompanying drawing illustrates in full color a typical leaf of this new plant variety, shows the ripe fruit as viewed from the stem end and in side view, and also shows the stone, with the stem still attached.

Throughout this specification, color names beginning with a small letter signify that the name of that color, as used in common speech, is aptly descriptive. Color names with capital letters designate values based upon the Nickerson Color Fan, put out by Munsell Color Co.

The tree is of medium size and normal vigor. It is upright-spreading, and tends to dense growth. It also tends to rounding of the head. Its hardiness has not been generally tested. The specimen grown at Wasco, Calif., was very productive, and bore regularly and heavily.

The trunk is of medium thickness, and has smooth to medium bark. The branches are medium in caliper and of moderate smoothness. They are dull in color, being between Moderate Brown, 7.5YR 4/5, and Grayish Brown, 7.5YR 3/2, as gauged by the Nickerson Color Fan. They carry numerous medium to small lenticels.

The leaves of this new variety would belong in Class IV of the Meader & Blake system, since they are "distinctly wavy and crinkled." They are from 6" to 6½" long, and 1¼"t o 1½" wide; they are acuminate, lanceloate in shape, of medium thickness and smooth. Their color on the upper side is between Moderate Olive Green, 5GY 4/3, and Moderate Olive Green, 7.5GY 4/4. On the under side, their color value lies between Moderate Olive Green, 2.5GY 4/3, and Moderate Olive Green, 5GY 4/3.

The leaf margin is glandular and finely serrate. The petiole is of medium length and medium thickness. There are usually 2 to 3 glands, though sometimes 4 to 5. They are disposed oppositely and alternately, and are of medium size, both globose and reniform, mixed. The color is near Strong Yellow, 5Y 7/10, and they are located on the margin of the leaf just above the petiole and on the petiole near the attachment of the leaf blade. The stipules are short and early deciduous.

The flower buds are large and long, being conic and pointed in shape, and also plump. They are not appressed.

The flowers first bloom, on the average, at about the first of March, at Wasco, Calif. They attain full bloom, on the average, at about the 13th of March. This is early or at least moderately early, in comparison with other varities. The flowers are light pink in color, of medium size and showy.

The fruit, as now described, was eaten ripe on the 24th of May. The size of the fruit at that stage of its development was medium and the fruits borne were relatively uniform in size, having an axial diameter of about 2½" and a transverse diameter, in the plane of the suture, of from 2½" to 2⅝". At right angles to the suture plane, the measurement was 2½" to 2¾", thus indicating a practically uniform globose shape.

The suture was an inconspicuous line extending from the base, but discontinuous at the apex. The ventral surface was rounded, with equal lips. The stem cavity was

[1] Meader & Blake: Progress Report on Identification of Peach Varieties by Leaf Characteristics, vol. 37 (1939 Proceedings) American Society for Horticultural Science, pages 203–207.

rounded, except that it was usually elongated in the plane of the suture, with the suture showing on both sides. The depth of the cavity was about ½", and its width about ⅞" to 1". The base of the fruit was rounded to truncate, and its apex, rounded to truncate with a short or even non-existent pistil point.

The stem is about ¼" to ⅜" long, of medium caliper and glabrous. It adheres rather weakly to the stone.

The skin, which was thin to medium in thickness and of medium texture, rested free upon the fruit when fully ripe, but had no tendency to crack. Its color ranged from Moderate Orange Yellow, 7.5YR 8/8, to Moderate Orange Yellow, 10YR 8/10, blushed with a color between Dark Reddish Orange, 7.5R 4/11, and Dark Red, 5R 3/7. The down was scant, and it did not roll up when rubbed.

The color of the flesh was near Moderate Orange Yellow, 10 YR 8/10, in general, but the surface of the pit cavity was near Vivid Yellow, 5Y 8/12. The amygdalin was scant, the juice abundant and rich. The texture was medium and melting, the fibers fine and tender. The flavor was marked by a good balance between sugar and acid. There was a pronounced aroma, and the fruit ripened evenly to produce a good eating quality.

The stone clings to the flesh over the entire surface. Its fibers are long. It is of medium size, being about 1¼" long, 1" broad, and ¾" thick. The form is generally ovoid but is cuneate toward the apex. The base is oblique, the hilum narrow, and oblong, and the apex is acuminate. The sides of the stone are slightly unequal, being curved on the right and left side. The surface of the sides is irregularly furrowed toward the apex, and pitted toward the base. The ridges are rounded toward the apex.

The pits are circular or elongated, having a ventral edge which is of medium thickness. They are without wing throughout. The dorsal edge is narrow, with deep narrow grooves and interrupted ridges on either side. The color of the stone is near Pale Orange Yellow, 7.5YR 9/4. The stone has little to no tendency to split.

The fruit is well adapted for market use and to serve as dessert. It has good keeping quality and good resistance to insects and diseases. Furthermore, it has good shipping quality.

I claim:

1. A new variety of peach tree, substantially as herein shown and described, manifesting in combination a plurality of the following features, namely, a vigorous upright-spreading habit of growth; leaves which are rather long and distinctly wavy and crinkled, and which bear a mixture of globose and reniform glands both on the petiole and on the margin of the leaf adjacent the petiole; a chilling requirement similar to that of the "Armgold" peach, a tendency to bear large crops of fruits which ripen early, at or about the same time as peaches of the "Armgold" variety, said fruits being substantially larger, however, than the "Armgold" fruits, though slightly smaller than peaches which ripen several weeks later; and the flesh of said fruits, until fully ripe, being closely adherent to the stone, but loosening somewhat when ripe, and being of melting texture, comparable to that of peaches which ripen in mid-season.

No references cited.

ROBERT E. BAGWILL, Primary Examiner